(12) United States Patent
Nathan et al.

(10) Patent No.: US 7,337,007 B2
(45) Date of Patent: *Feb. 26, 2008

(54) SURFACE NEUROPROSTHETIC DEVICE HAVING A LOCATING SYSTEM

(75) Inventors: Roger H. Nathan, Herzilia B (IL); Amit Dar, Ramot Hashavim (IL)

(73) Assignee: Ness Neuromuscular Electrical Stimulation Systems Ltd., Ra'Anana (IL)

( * ) Notice: Subject to any disclaimer, the term of this patent is extended or adjusted under 35 U.S.C. 154(b) by 675 days.

This patent is subject to a terminal disclaimer.

(21) Appl. No.: 10/222,878

(22) Filed: Aug. 19, 2002

(65) Prior Publication Data

US 2003/0114893 A1 Jun. 19, 2003

Related U.S. Application Data

(60) Provisional application No. 60/340,277, filed on Dec. 18, 2001.

(51) Int. Cl.
*A61N 1/36* (2006.01)

(52) U.S. Cl. .................. 607/48; 607/149; 607/49; 602/2

(58) Field of Classification Search .............. 607/48, 607/149, 49; 602/26, 23, 2; 623/901, 909
See application file for complete search history.

(56) References Cited

U.S. PATENT DOCUMENTS

| | | | | |
|---|---|---|---|---|
| 4,432,368 A | | 2/1984 | Russek | |
| 4,704,129 A | * | 11/1987 | Massey | 623/25 |
| 5,330,516 A | | 7/1994 | Nathan | |
| 5,562,707 A | * | 10/1996 | Prochazka et al. | 607/2 |
| 5,628,722 A | * | 5/1997 | Solomonow et al. | 602/26 |
| 5,643,332 A | | 7/1997 | Stein | |
| 6,064,912 A | * | 5/2000 | Kenney | 607/48 |
| 6,456,885 B1 | * | 9/2002 | Shiba et al. | 607/48 |

* cited by examiner

*Primary Examiner*—George R. Evanisko
*Assistant Examiner*—Michael Kahelin
(74) *Attorney, Agent, or Firm*—Mark M Friedman

(57) ABSTRACT

A surface neuroprosthetic device for functional electrical stimulation (FES) having a locating system for locating the device on to a limb segment of a user, and a method therefor, the device including: (a) an at least semi-rigid exoskeleton shell for encompassing at least a portion of the limb segment; (b) at least one electrical stimulation electrode operatively connected with the shell, for making electrical contact with a surface of the limb segment, so as to effect FES of at least one muscle of the limb segment; and (c) a locator, operatively connected with the shell, for determining a positioning of the shell relative to the limb segment, such that the electrode is positioned near an activating point, the locator including: (i) means for determining rotational positioning of the exoskeleton shell on the limb segment, and (ii) means for determining longitudinal positioning of the exoskeleton shell on the limb segment.

27 Claims, 9 Drawing Sheets

SURFACE NEUROPROSTHETIC DEVICE HAVING A LOCATING SYSTEM

This application draws priority from U.S. Provisional Patent Application Ser. No. 60/340,277, filed Dec. 18, 2001.

FIELD AND BACKGROUND OF THE INVENTION

The present invention relates to a surface neuroprosthetic device for Functional Electrical Stimulation (FES) of impaired limbs, and more particularly, to a surface neuroprosthetic device having a locating system for accurate, facile, and repeatable locating of the device on to the limb, and the device electrodes on to the motor points of the muscles thereof.

FES is a means to communicate with the neuromuscular system for producing contraction in muscles or sensory input to the body. FES is used in neuroprostheses for restoring active function to paralyzed or plegic body limbs in patients suffering disease or trauma to the central nervous system, in neurological conditions such as stroke, spinal cord injury, head injury, cerebral palsy and multiple sclerosis. Surface FES systems use controlled electrical currents through electrodes placed on the surface of the body, in order to trigger contraction from muscles underlying the electrode or to input sensory stimulus. Surface neuroprostheses can coordinate the FES-activation of several muscles of the limb alone, or in coordination with voluntary activation of muscles under natural neurological control. Surface neuroprostheses are in use today for functional activities such as walking, standing, gripping/releasing objects, etc.

Electrode placement is an important issue for surface neuroprostheses. The patient or his caretaker is required to set up the neuroprosthesis each time he wishes to use it. This involves ensuring that all the electrodes are positioned accurately over the motor points of the muscles to be activated. Accurate electrode positioning ensures activation of the correct muscle without overflow to unwanted muscles, sensory tolerance of the stimulation current intensity needed to produce the desired response, and the quality of the muscle contraction. A critical factor in surface neuroprosthesis design is the provision of a means to reduce the prohibitive time and high expertise required to position the array of electrodes required to produce complex movement patterns.

Accurate electrode positioning has proved a barrier to the use of this technology and has, to date, limited the use of the surface neuroprosthesis.

In order to position an exoskeleton on to a body site (also referred to herein as "limb") quickly, accurately and repeatedly, some means must be provided to ensure correct position and orientation of the exoskeleton relative to the body site. We refer to this means as a "locator".

Ordinarily, devices that conform to the shape of a particular body site enable more facile positioning of the electrodes over the activation points. U.S. Pat. No. 4,432,368 to Russek describes a locator for a transcutaneous nerve stimulation (TENS) device for applying sensory FES to the lower back region, in order to provide pain relief. The electrodes are mounted on a garment which itself locates by tactile feedback on to bony landmarks: the iliac crest and the sacro-coccygeal joint. The sacro-coccygeal landmark is outside the visual field of the device user, and tactile feedback is the means used for locating the device.

U.S. Pat. No. 5,643,332 to Stein discloses a surface neuroprosthesis device for the lower limb, in which a band housing the device components is placed on to the lower leg and is located on to the tibia by a V-shaped metal plate used to position the device in a circumferential fashion. The locator angle can be bent during the initial device set-up session to fit individual patients. No longitudinal location of the V-shaped metal plate is provided for positioning the device along the longitudinal axis of the limb.

U.S. Pat. No. 5,330,516 to Nathan describes an upper limb neuroprosthesis locator. The device includes a semi-rigid exoskeleton whereby the surface electrodes are carefully positioned, by an expert, within the inside surface of the exoskeleton during an initial fitting session. Subsequently, the device user places the exoskeleton on to his arm, locating, firstly, the distal spiral portion of the device on to the bony mass of his hand, and then placing the proximal portion of the device around his forearm. The entire electrode array is constrained for accurate positioning over the limb surface, according to the electrode placement of the expert. The spiral locator allows this accurate donning of the electrode array by utilizing the underlying bone structure of the forearm and hand.

Both the leg device disclose by Stein in U.S. Pat. No. 5,643,332 and the upper limb device of Nathan (U.S. Pat. No. 5,330,516) require initial device set-up to be carried out by an expert, who positions the electrodes in the device to elicit optimal muscle contraction from the individual patient. The electrode positioning procedure requires a high degree of skill in the art in order to set up a full electrode array in an optimal manner. It would be advantageous to have a device and a method of implementing the device, which allow the surface electrode array to be manufactured in a fixed position within the device. This enables pre-arranging the surface electrode array optimally, one electrode with respect to each other, and reduces the dependence on the high degree of skill, artistry, and experience required of the clinician to carry out the initial electrode set-up procedure. The initial device set-up procedure would now be reversed with respect to the prior art: the device housing the entire electrode array is placed on the limb and adjusted to the optimal position, then locator system is positioned and attached to the device, such that the device can be repeatably located to this optimal position by the patient. This would require the provision of fast accurate means for positioning the device longitudinally as well as circumferentially on to a conical upper or lower limb segment.

It is thus manifest that fast and accurate electrode positioning has proved to be a problematic issue of central importance to the implementation of surface neuroprostheses. Moreover, neurological deficits such as perceptual or motor deficiencies may affect the requirements of the locator system.

Perceptual difficulties in neurological conditions such as stroke can often present a challenge to recognition of device orientation in space relative to the limb. Here the problem is to provide a means for making the device orientation and any rotation-maneuver required for donning the device on a limb "obvious", fast and easy.

In addition, motor deficiency can take the form of limb weakness, paralysis or spasticity, which make donning the device a challenge. In hemiplegia resulting from stroke or brain injury, the side of the body on which the neuroprosthesis is donned is often plegic. The donning action must often be carried out using solely the contra-lateral non-plegic hand. The posture of plegic limb is often problematic where spasticity results in reduced voluntary movements and also limited passive mobility of the limb. The limb can be set at the extreme of its range of motion, for example, full adduction at the shoulder joint resulting in the upper arm being held tightly against the trunk. This abnormal limb posture and lack of limb mobility can present biomechanical problems in donning the device and locating it on to the limb.

It is further noted that the limitations and deficiencies of known surface neuroprostheses devices are particularly glaring regarding upper-arm surface neuroprosthesis applications. To the best of our knowledge, no upper-arm surface neuroprosthesis device has been successfully developed heretofore.

There is therefore a recognized need for, and it would be highly advantageous to have, a neuroprosthetic device and method for functional electrical stimulation of impaired limbs having a reliable locating system that provides for accurate, facile, simple, fast and repeatable positioning and orientation of the device over the activation points of the muscles, such that the FES is effective and comfortable.

SUMMARY OF THE INVENTION

The present invention is a neuroprosthetic device for functional electrical stimulation of impaired limbs having a locating system for accurate, facile, and repeatable positioning of the device on the activating points of the muscles.

According to the teachings of the present invention there is provided a surface neuroprosthetic device for functional electrical stimulation having a locating system for locating the device on to a limb segment of a user, the device including: (a) an at least semi-rigid exoskeleton shell for encompassing at least a portion of the limb segment; (b) at least one electrical stimulation electrode operatively connected with the shell, the electrode for making electrical contact with a surface of the limb segment, so as to effect functional electrical stimulation (FES) of at least one muscle of the limb segment; and (c) a locator, operatively connected with the shell, for determining a positioning of the shell relative to the limb segment, such that the electrode is positioned near an activating point of the muscle, the locator including: (i) means for determining rotational positioning of the exoskeleton shell on the limb segment, and (ii) means for determining longitudinal positioning of the exoskeleton shell on the limb segment.

According to another aspect of the present invention there is provided a surface neuroprosthetic device for (FES) having a locating system for locating the device on to a limb segment of a user, the device including: (a) an at least semi-rigid exoskeleton shell for encompassing at least a portion of the limb segment; (b) a surface electrode array fixed in position within the shell, the electrode array for making electrical contact with a surface of the limb segment, so as to effect functional electrical stimulation of the limb segment; and (c) a locating system, operatively connected with the shell, for identifying the orientation of the device, determining a positioning of the shell relative to the limb segment, and facilitating donning of the device at a correct position and orientation on to the limb segment, the locating system including: (i) means for determining rotational positioning of the exoskeleton shell on the limb segment, and (ii) means for determining longitudinal positioning of the exoskeleton shell on the limb segment, the locating system being adjusted and attached to the device during an initial device set-up session to fit the limb segment of the user.

According to another aspect of the present invention there is provided a method of locating a neuroprosthetic device on a limb segment of a user, the method including the steps of: (a) providing a neuroprosthetic device including: (i) an at least semi-rigid exoskeleton shell for encompassing at least a portion of the limb segment; (ii) at least one electrical stimulation electrode operatively connected with the shell, the electrode for making electrical contact with a surface of the limb segment, so as to effect functional electrical stimulation (FES) of at least one muscle of the limb segment; and (iii) a locating system for positioning the shell relative to the limb segment, the locating system including: (A) means for determining rotational positioning of the exoskeleton shell on the limb segment, and (B) means for determining longitudinal positioning of the exoskeleton shell on the limb segment; (b) donning the neuroprosthetic device on the limb segment; (c) applying the means for determining rotational positioning such that the neuroprosthetic device is rotationally positioned near an activating point on the limb segment, and (d) applying the means for determining longitudinal positioning such that the neuroprosthetic device is longitudinally positioned near the activating point on the limb segment.

According to another aspect of the present invention there is provided a of locating a neuroprosthetic device on a limb segment of a user, the method including the steps of: (a) providing a neuroprosthetic device including: (i) an at least semi-rigid exoskeleton shell for encompassing at least a portion of the limb segment; (ii) a surface electrode array fixed in position within the shell, the electrode array for making electrical contact with a surface of the limb segment, so as to effect functional electrical stimulation (FES) of the limb segment, and (iii) a locating system, operatively connected with the shell, the locating system including: (A) means for determining rotational positioning of the exoskeleton shell on the limb segment; (b) adjusting and attaching the locating system to the device during an initial device set-up session, so as to position the neuroprosthetic device to activate effectively the limb segment of the user; (c) subsequently donning the neuroprosthetic device on the limb segment, and (d) applying the means for determining rotational positioning such that the exoskeleton shell and fixed electrode array is rotationally positioned to activate effectively the limb segment of the user.

According to features in the described preferred embodiments, the locator further includes means for differentiating between a front side and a rear side of the shell and for identifying an orientation of the device.

According to further features in the described preferred embodiments, the locator further includes: (iii) means for differentiating between upper and lower edges of the exoskeleton shell.

According to further features in the described preferred embodiments, the means for determining rotational positioning include a handle for gripping the device, the handle defining an orientation of the device, such that a natural donning motion of a hand holding the handle sets the device in an approximately correct rotational orientation on the limb segment.

According to further features in the described preferred embodiments, the means for determining longitudinal positioning include a handle for gripping the device, the handle defining a position of the device along the limb segment, such that a natural donning motion of a hand holding the handle sets the device in an approximately correct longitudinal position along the limb segment.

According to further features in the described preferred embodiments, the means for differentiating between the front side and rear side of the shell include at least one visual cue.

According to further features in the described preferred embodiments, the at least one visual cue includes an edge of the front side and an edge of the rear side, each edge having a characteristically different curvilinearity.

According to further features in the described preferred embodiments, the edge of the front side is generally concave, and the edge of the rear side is generally convex.

According to further features in the described preferred embodiments, the means for differentiating between a front side and a rear side of the shell and for identifying an orientation of the device include at least one visual cue selected from the group consisting of colored designs, markings, and logos.

According to further features in the described preferred embodiments, the means for differentiating between the upper and lower edges include at least one flap extending from the shell.

According to further features in the described preferred embodiments, the means for determining rotational positioning of the exoskeleton shell on the limb segment include flaps longitudinally extending from the shell.

According to further features in the described preferred embodiments, the flaps are configured so as to contact surface of the limb segment when the device is correctly positioned on the limb segment.

According to further features in the described preferred embodiments, the flaps are configured so as to snugly contact surface of the limb segment when the electrode is in a correct position near the activating point and such that rotation of the device away from the position results in a visually detectable deflection of the flaps According to further features in the described preferred embodiments, the flaps are configured so as to snugly contact surface of the limb segment when the electrode is in a correct position near the activating point and such that rotation of the device away from the correct position generates a mechanical torsion resistance for guiding the user.

According to further features in the described preferred embodiments, the flaps are disposed in slots in the shell.

According to further features in the described preferred embodiments, the flaps are disposed in the slots in a reversibly detachable fashion.

According to further features in the described preferred embodiments, the flaps are designed and configured to be extended from the shell into an extended position during donning, and to be retracted towards the shell into a retracted position during use of the device.

According to further features in the described preferred embodiments, the shell further including securing means for securing the flaps in the retracted position.

According to further features in the described preferred embodiments, the exoskeleton shell is designed to encompass at least a portion of an upper arm, the locating system further including: (iii) flaps extending from the shell towards an elbow of the arm, the flaps for locating the exoskeleton shell on each side of the elbow.

According to further features in the described preferred embodiments, the exoskeleton shell is designed to encompass at least a portion of a lower leg, the locating system further including: (iii) flaps extending from the shell towards a knee joint, the flaps for locating the exoskeleton shell on each side of the knee joint.

According to further features in the described preferred embodiments, the exoskeleton shell is designed to encompass at least a portion of a lower leg, and wherein the means for determining rotational positioning include a mold in the shell, the mold having a shape corresponding to an inferior surface of a tibial tuberocity of the lower leg, the mold for aligning with the tibial tuberocity to determine the rotational positioning of the shell on the lower leg.

According to further features in the described preferred embodiments, the exoskeleton shell is designed to encompass at least a portion of a lower leg, and wherein the means for determining longitudinal positioning include a mold in the shell, the mold having a shape corresponding to an inferior surface of a tibial tuberocity of the lower leg, the mold for aligning with the tibial tuberocity to determine the longitudinal positioning of the shell on the lower leg.

According to further features in the described preferred embodiments, the exoskeleton shell is designed to encompass at least a portion of a lower leg, and wherein the means for determining rotational positioning and the means for determining longitudinal positioning include a mold in the shell, the mold having a shape corresponding to an inferior border of a patella of the lower leg, the mold for abutting with the inferior border to determine the rotational positioning and the longitudinal positioning of the shell on the lower leg.

According to further features in the described preferred embodiments, the mold has an adjusting and attaching means such that the mold may be adjusted to an optimal position to suit an individual patient and then attached in this position to the shell for subsequent location of the device by the patient on to the limb segment of the patient.

According to further features in the described preferred embodiments, the exoskeleton shell is designed to encompass at least a portion of a lower leg, and wherein the means for rotational positioning and the means for longitudinal positioning include at least one long flap extending down from the shell and over a malleolus of an ankle joint of the leg, so as to determine the rotational positioning and the longitudinal positioning of the shell on the leg.

According to further features in the described preferred embodiments, the long flap has an adjusting and fixing means such that the mold may be adjusted to an optimal position to suit an individual patient and then attached in this position to the shell for subsequent location of the device by the patient on to his limb segment.

According to further features in the described preferred embodiments, the exoskeleton shell is designed to encompass at least a portion of a thigh, and the means for rotational positioning include a flat locator surface disposed on a posterior exterior surface of the shell, the flat locator surface for aligning with a flat seat on which the user is seated during donning of the device.

According to further features in the described preferred embodiments, the exoskeleton shell is designed to encompass at least a portion of a forearm, and the means for rotational positioning include a flat locator surface disposed on an exterior palmar surface of the shell, the flat locator surface for aligning with a flat reference surface during donning of the device while aligning, to the flat reference surface, a plane of a palm of a hand of the forearm.

According to further features in the described preferred embodiments, the shell and the slots are designed such that the flaps are for attaching to, and extending from, either longitudinal side of the shell, thereby enabling utilization of the device in both left-limb and right-limb applications.

According to further features in the described preferred embodiments, the neuroprosthetic device further includes: (iv) a handle for gripping the device, the handle defining an orientation of the device, such that a natural donning motion of a hand holding the handle sets the device in an approximately correct rotational position on the limb segment, wherein step (b) is performed by means of the handle, so as to set the device in the approximately correct rotational position.

According to further features in the described preferred embodiments, the locating system further includes flaps longitudinally extending from the shell.

According to further features in the described preferred embodiments, the flaps are configured so as to contact surface of the limb segment, the method further including the step of: (e) rotating the device in a vicinity of a potentially correct position on the limb segment.

According to further features in the described preferred embodiments, the method further includes the step of: (f) if rotating the device results in substantially zero mechanical torsion resistance, identifying the position as a correct rotational position.

According to further features in the described preferred embodiments, the method further includes the step of: (g) if rotating the device results in mechanical torsion resistance, reapplying step (c).

According to further features in the described preferred embodiments, method of further includes the step of: (g) if rotating the device results in the flaps deflecting outwards, reapplying step (c).

According to further features in the described preferred embodiments, the exoskeleton shell is designed to encompass at least a portion of a lower leg.

According to further features in the described preferred embodiments, the means for determining rotational positioning include at least two flaps longitudinally extending from the shell, and the limb segment belongs to an upper arm.

According to further features in the described preferred embodiments, step (c) includes rotating an elbow joint of the arm from extension to flexion, and wherein, when the device is rotationally aligned, proximal forearm tissue on the arm contacts the two flaps.

According to further features in the described preferred embodiments, the limb segment belongs to an upper an, the means for determining longitudinal positioning including at least two flaps longitudinally extending from the shell, wherein the flaps extend down from the shell and relate to epicondyles of an elbow of the arm to establish a longitudinal position along a long axis of the device.

According to further features in the described preferred embodiments, step (c) includes rotating an elbow joint of the arm from extension to flexion, wherein, when the device is incorrectly positioned, a flexing of the elbow causes at least one of the flaps to be deflected outwards away from the limb segment by soft tissue of a proximal forearm associated with the upper arm.

According to further features in the described preferred embodiments, the the limb segment belongs to a lower leg, wherein a mold in the shell has a shape corresponding to an inferior surface of a tibial tuberocity of the leg, and wherein step (c) includes aligning the mold with the tibial tuberocity to establish rotational positioning of the shell on the leg.

According to further features in the described preferred embodiments, the step (d) includes aligning the mold with the tibial tuberocity to establish longitudinal positioning of the shell on the leg.

According to further features in the described preferred embodiments, the limb segment belongs to a lower leg, wherein a mold in the shell has a shape corresponding to an inferior surface of a tibial tuberocity of the leg, and wherein step (d) includes aligning the mold with the tibial tuberocity to establish longitudinal positioning of the shell on the leg.

According to further features in the described preferred embodiments, the limb segment belongs to a lower leg, wherein a mold in the shell has a shape corresponding to an inferior border of a patella of the leg, and wherein step (c) includes abutting the inferior border with the mold to establish rotational positioning of the shell on the leg.

According to further features in the described preferred embodiments, the wherein the limb segment belongs to a lower leg, wherein a mold in the shell has a shape corresponding to an inferior border of a patella of the leg, and wherein step (d) includes abutting the inferior border with the mold to establish longitudinal positioning of the shell on the leg.

According to further features in the described preferred embodiments, the limb segment belongs to a lower leg, wherein the means for rotational positioning and the means for longitudinal positioning include at least one long flap extending down from the shell and over a malleolus of an ankle joint of the leg, and wherein step (c) and step (d) include aligning the flap with the malleolus to establish rotational and longitudinal positioning of the shell on the leg.

According to further features in the described preferred embodiments, the limb segment is a thigh segment, wherein the exoskeleton shell encompasses at least a portion of the thigh segment, and wherein the means for rotational positioning include a flat locator surface disposed on a posterior exterior surface of the shell, the method further including the step of: (e) sitting the user on a flat seat in a predetermined seating posture during the donning of the device, such that the flat locator surface contacts the flat seat, wherein step (e) includes aligning the flat locator surface with the flat seat to establish rotational positioning of the shell on the upper leg.

According to further features in the described preferred embodiments, the limb segment belongs to a forearm, wherein the exoskeleton shell encompasses at least a portion of the forearm, and wherein the means for rotational positioning include a flat locator surface disposed on a posterior exterior surface of the shell, wherein step (c) includes resting a palm of a hand of the forearm on to the flat surface and aligning the flat locator surface and the palm with the flat surface to establish rotational positioning of the shell on the forearm.

According to further features in the described preferred embodiments, locating system further includes: (B) means for determining longitudinal positioning of the exoskeleton shell on the limb segment; the method further including the steps of: (e) applying the means for determining longitudinal positioning such that the exoskeleton shell and the fixed electrode array are longitudinally positioned to activate effectively the limb segment of the user.

As used herein in the specification and in the claims section that follows, the term "activation point" and the like refer to a location on a limb for receiving current from a surface electrode, so as to achieve functional electrical stimulation. It must be emphasized that the position and nature of the activation points depend on the individual patient and on the judgment of the clinician setting up the device. Electrodes may be positioned directly on the muscle motor points, or at some distance from the motor points over regions of the muscle body where the response to FES may be less strong, but more stable. The electrode may even be positioned over non-excitable motor regions where motor response is avoided, for example to elicit a sensory stimulation input only to the limb.

Sensors in the neuroprosthesis may also affect the positioning of the neuroprosthesis on the limb. Here the positioning of the neuroprosthesis on the limb, and hence the sensor, may be critical in monitoring the response of the limb to the limb activation.

The structure of the neuroprosthesis is also required to locate on to the limb in the position and orientation such that the device is self-supporting in a mechanically stable fashion on the limb even during dynamic limb articulations.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
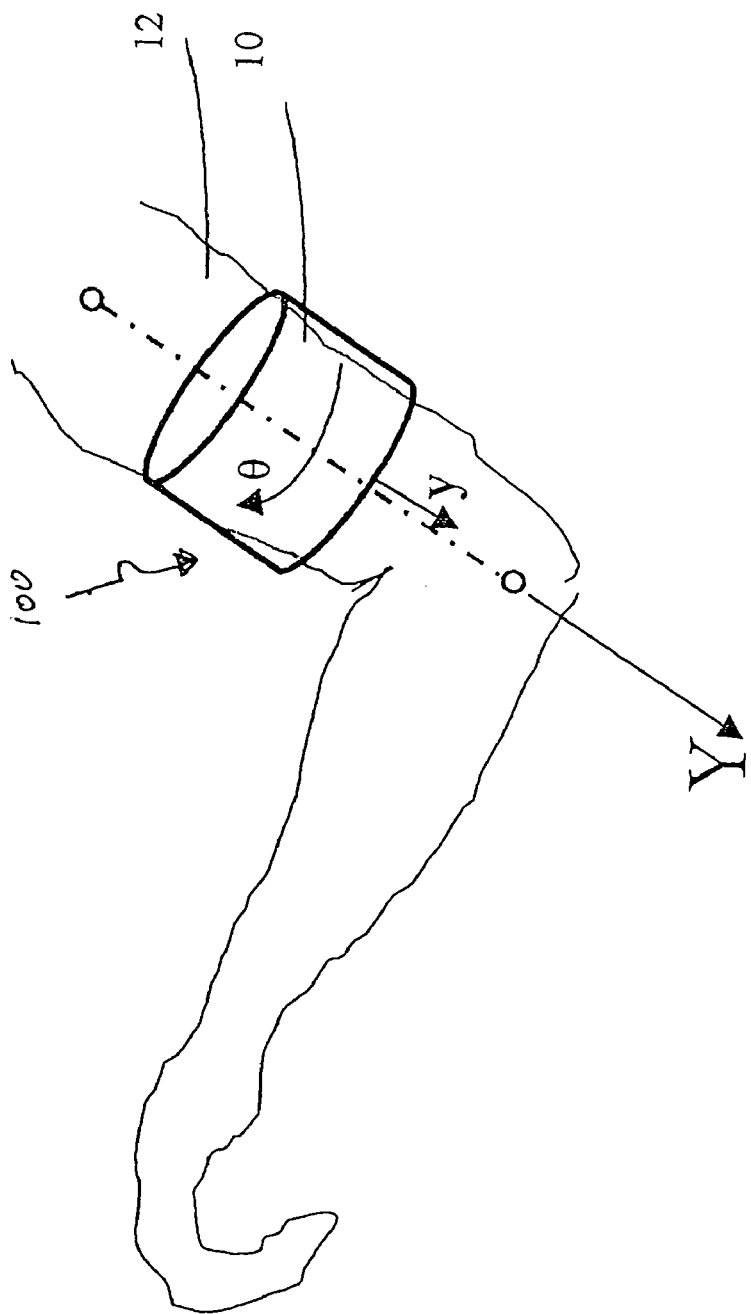
FIG. 1 is a schematic diagram of a generic exoskeleton device encompassing an upper limb.

The present invention is a neuroprosthetic device for functional electrical stimulation of impaired limbs having a locating system for accurate, facile, and repeatable positioning of the device on the activating points of the muscles.

As used herein in the specifications and in the claims section that follows, the term "locating system" or "locator" refers to a system for accurate, fast and repeatable positioning of a FES device on the limb of a patient. The locating system assures correct position and orientation of a rigid or semi-rigid exoskeleton relative to the limb, thereby positioning the electrodes integrated into the device in an accurate, fast and repeatable manner over the sites selected to activate the limb muscles.

The principles and operation of the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. Locating rigid or semi-rigid exoskeleton FES devices on a limb of a user depends on the specific limb and requires a specific locator that fits the shape and size of the limb. Usually, locators rely on mechanical and physical positioning of the device on a mechanical stable feature of the particular limb segment. Typical examples are skeletal and bony features underlying the skin surface, and the axis of rotation of limb joints having one degree of freedom, such as the elbow or knee.

FES devices for upper or lower limb segments are basically tubular in shape, in order to conform to the substantially conical shape of these limb segments. Referring now to the drawings, FIG. 1 schematically shows a neuroprosthetic device 100 placed on an upper arm segment 12, as a typical example of a limb segment. Exoskeleton 10 is positioned so as to encompass upper arm segment 12. The conical form of upper arm segment 12 interacts with the tubular form of exoskeleton 10. The number of degrees of freedom remaining between exoskeleton 10 and arm 12 are reduced to 2, fixing the position and orientation of exoskeleton 10 in all but the angular orientation θ of exoskeleton 10 about the long Y-axis of upper arm segment 12, and the positional location y of exoskeleton 10 along the long Y-axis of upper arm segment 12.

The sensitivity of FES device performance to location on the limb, and particularly to these two degrees of freedom about the long axis of the limb, is the essence of the problem in the donning of the device by the user (or by the patient caretaker or family member) to the limb of the user. Each limb segment has its own specific anatomical features that might be used for the device location. Each device user may have disabilities that make the device donning a particular challenge. The neurological deficits, mentioned hereinabove, such as perceptual or motor deficiencies, may affect the requirements of the locating system.

The locating system of the present invention includes several components, integrated into the FES neuroprosthetic device, for facilitating each stage of the donning process, and for overcoming the various motor and perceptual challenges of the user.

One component of the locating system is a geometrical design of the device especially suitable for users who may be perceptually challenged. Here, the shape of the device simplifies identification of device orientation prior to donning, to enable the device to be placed right side up, and generally facing the right direction.

In addition, a handle is provided to grip the device in order to place it on to the plegic limb. The handle defines the orientation of the device such that when holding the device by the handle of the locator, and by carrying out a natural motion to bring the device to the plegic limb, the device immediately locates on to the limb in approximately the correct position and orientation.

Specific components of the locating system enable accurate positional adjustment of the device along the long axis of the limb, while other components enable accurate adjustment of the angular orientation of the device about the long axis of the limb.

During initial setting-up of the neuroprosthesis, the clinician may select or adjust one or more locating means appropriate for a particular patient. The clinician is not required to adjust the electrode array. Subsequently, each time the patient places the device on his arm, the device aligns approximately along the limb segment in approximately the correct location. The patient then adjusts the position of the device along the length of the segment, and the orientation of the device around the segment using this combination of visual, mechanical and tactile cues provided by the locating system.

Figure 2:
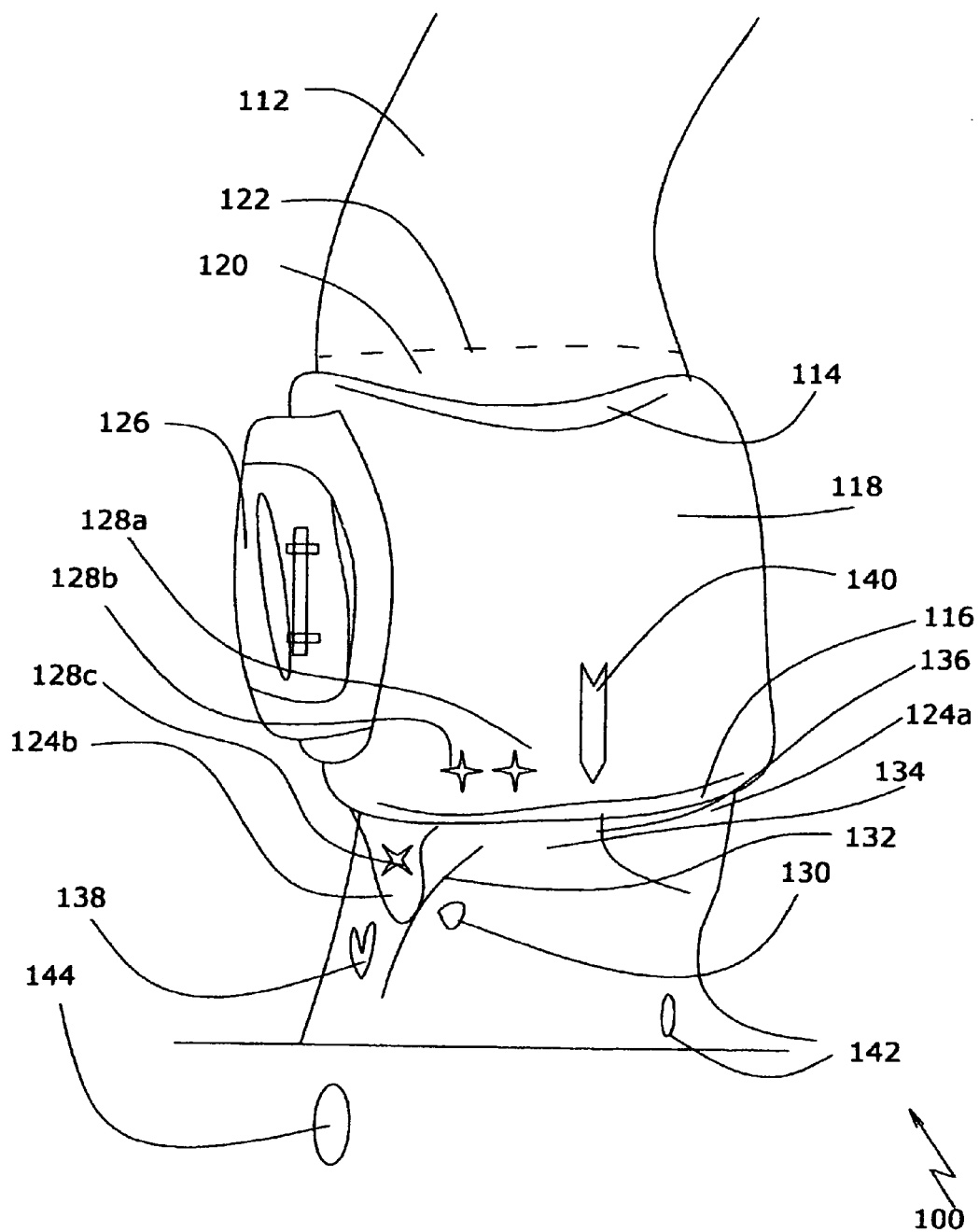
FIG. 2 is a perspective front view of an upper arm neuroprosthetic device having a locating system, and disposed on an upper arm, according to one aspect of the present invention.

FIG. 2 provides a perspective view of an upper arm neuroprosthetic device equipped with a locating system, according to one aspect of the present invention. The locating system, of this preferred embodiment, includes various visual and mechanical components that facilitate the identification of the general orientation of the device before donning. In this drawing of upper arm neuroprosthetic device 100, upper concave curved edge 114 and lower concave curved edge 116 are visual cues used to identify the front panel 118 of device 100, and to differentiate from the rear panel 120, which has convex-shaped edges 122. These cues allow a perceptually challenged user to identify between the front and rear of device 100.

Flaps 124a and 124b extend down from lower edge 116 of anterior panel 118 to further aid the perceptually challenged user to identify between the upper (proximal) edge 114 and lower (distal) edge 116 of device 100. Flaps 124a and 124b form, along with lower edge 116, an easily identifiable arch.

An additional visual cue for identifying, prior to donning, the orientation of device 100, is a handle 126 that identifies a lateral side of device 100. Handle 126 is positioned on device 100 so as to provide visual and tactile aid for the location of device 100 on the arm using the contra-lateral hand to hold handle 126.

Device 100, as shown in FIG. 2, is intended for a right upper arm, therefore handle 126 is held by the left hand as device 100 is donned. Keeping the elbow close to the body and bringing device 100 around and in front of the body, the natural trajectory introduces device 100 to the plegic arm at approximately the right position and orientation on upper arm segment 112. Handle 126 now acts as a mechanical locator within the neuroprosthesis system.

Device 100 is now approximately in position on upper arm segment 112. Components of the locating system are next used to more accurately position device 100 on the limb. Several components of the locating system, when used together, improve simplicity, speed and accuracy of the donning of device 100.

The arch, formed by flaps 124a and 124b together with lower concave curved edge 116, fits snugly around the distal anterior portion of upper arm segment 112. The arch, and particularly flaps 124a and 124b, provide a combination of mechanical constraint and visual assessment to accurately align device 100. When correctly aligned, flaps 124a and 124b lie snugly against the skin at the distal end of upper arm segment 112 along the lateral and medial sides. Any rotation of device 100, internally or externally, results in mechanical torsion resistance from one of flaps 124a and 124b as it interacts with arm tissue from upper arm segment 112, bending flap 124a and 124b out and pressing the tissue in. When rotated too much the other way, the torsional resistance reverses. When oriented correctly, torsional resistance for small rotations of device 100 is substantially zero.

The arch also presents visual feedback to the device user of device 100 when rotated out of position. When out of rotational alignment, flaps 124a and 124b do not lie snugly against the skin surface, rather, a gap appears between at least one of flaps 124a or 124b and the skin surface of the arm. This gap is easily identified and corrected by the user.

Further mechanical and visual feedback may be obtained from alignment with respect to the axis of rotation of a limb joint having one degree of freedom, which in FIG. 2, is the rotation of the elbow joint. As the joint is rotated from extension to flexion, the soft tissue of the forearm segment enters between flaps 124a and 124b. When device 100 is correctly aligned on the upper arm 112, the tissue of the proximal forearm segment lightly touches both flaps 124a and 124b. Any rotational misalignment of device 100 on the upper arm 112 results in interacting of flap 124a or 124b with the forearm tissue, bending outwards and lifting up. The interaction between the flaps 124a and 124b and the tissue during elbow joint flexion presents a clear visual cue to the user of a device rotational orientation on the upper arm segment 112.

Around the arch (formed by flaps 124a and 124b with lower edge 116 of front panel 118), markers 128a, 128b and 128c, are positioned by a clinician during the set-up of device 100 to indicate with visual cue alignments to features on the skin surface. Markers 128a, 128b and 128c are placed next to surface markings on the skin, or local visible anatomical features underlying the skin surface to locate and align device 100. Typical markings that may be selected from the limb site are natural markings on the skin surface such as beauty spots 130, skin creases 132 or anatomical features visible through the skin for example veins 134 or tendons 136. Where natural markings are absent, marks may be added to the body, such as by a skin marker or tattoo 138. Additionally, the centerline 140 of device 100 may be indicated on the arch to further help in positioning device 100.

Where appropriate, palpable bony landmarks can provide the user of device 100 with further tactile cues for accurate alignment of device 100. For example, the medial 142 and lateral 144 epicondyles of the humerus underlie flaps 124a and 124b. The fingertips may be used to judge the distance between the medial epicondyle 142 and flap 124a, and between the lateral epicondyle 144 and flap 124b. The relative positions thereof can be accurately assessed, and fine adjustment of the location of device 100 can be carried out accordingly.

Figure 3:
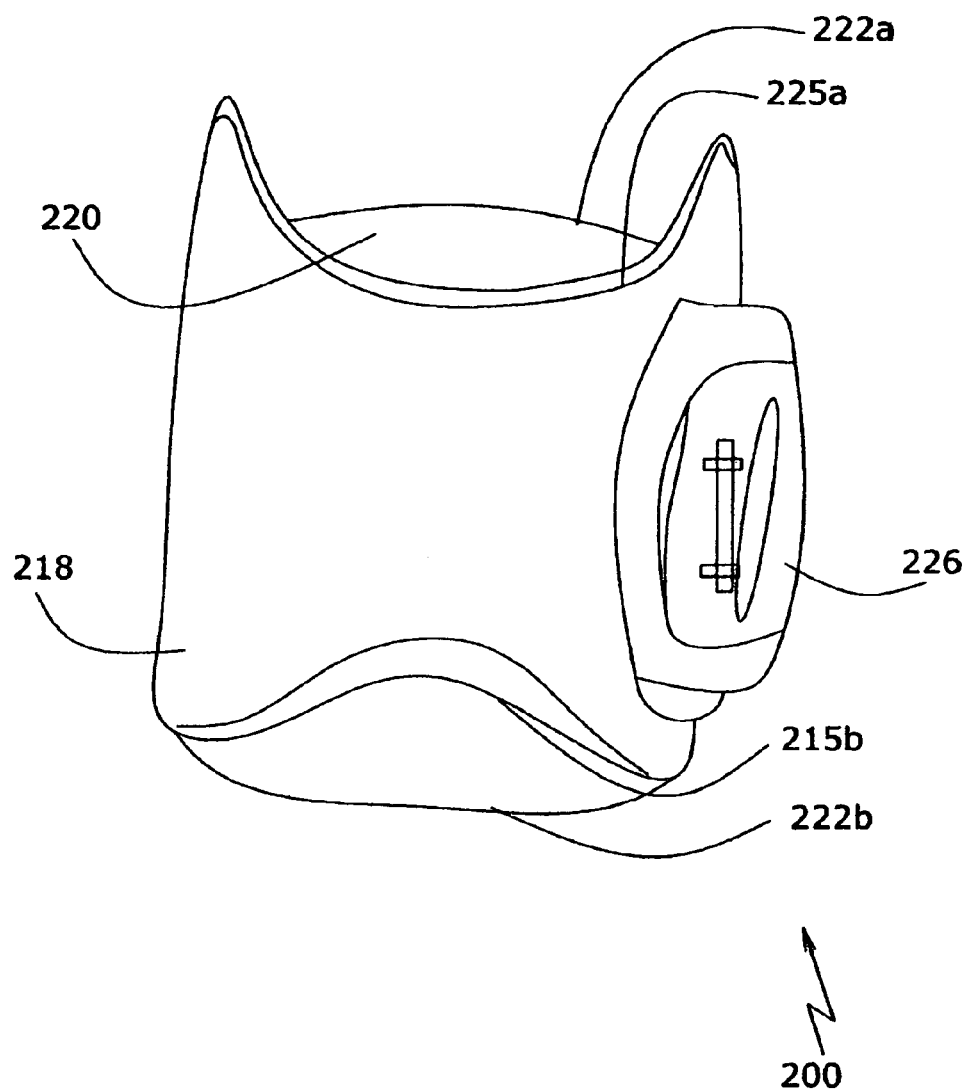
FIG. 3 is a perspective side view of an inventive lower leg neuroprosthetic device having a locating system.

Another preferred embodiment of the present invention, a neuroprosthetic leg device 200 for the lower leg, is illustrated in FIG. 3. Neuroprosthetic leg device 200, which, by way of example, is for a right leg, is worn at the proximal end of the lower leg segment (see FIG. 4). In a fashion that is similar to that of FES device 100 for the upper arm (shown in FIG. 2), local site anatomical features and bio-mechanical characteristics are used to locate leg device 200 on to the leg segment, including the general conical shape of the limb, local visible and palpable features in the vicinity, as well as the rotational axis of the knee joint.

For a perceptually challenged user of leg device 200, visual cues are integrated into the appearance of device 200 to make obvious the orientation of the device. Front and rear panels 218 and 220, respectively, are distinguished by characteristic shapes of convex edges 222a and 222b on the rear panel, and concave edges 215a and 215b on the front panel, as well as by colored designs, markings and logos to give visual orientation and to distinguish between the front and back and the top and the bottom of the device. A handle 226 on the medial side of leg device 200 serves to visually identify the medial side. In addition, for hemiplegic users, when grasped in the hand on the non-plegic side of the seated body, leg device 200 is brought around and on to the leg following the natural trajectory of the hand, reaching an approximately correct location of leg device 200 on the leg.

Figure 4:
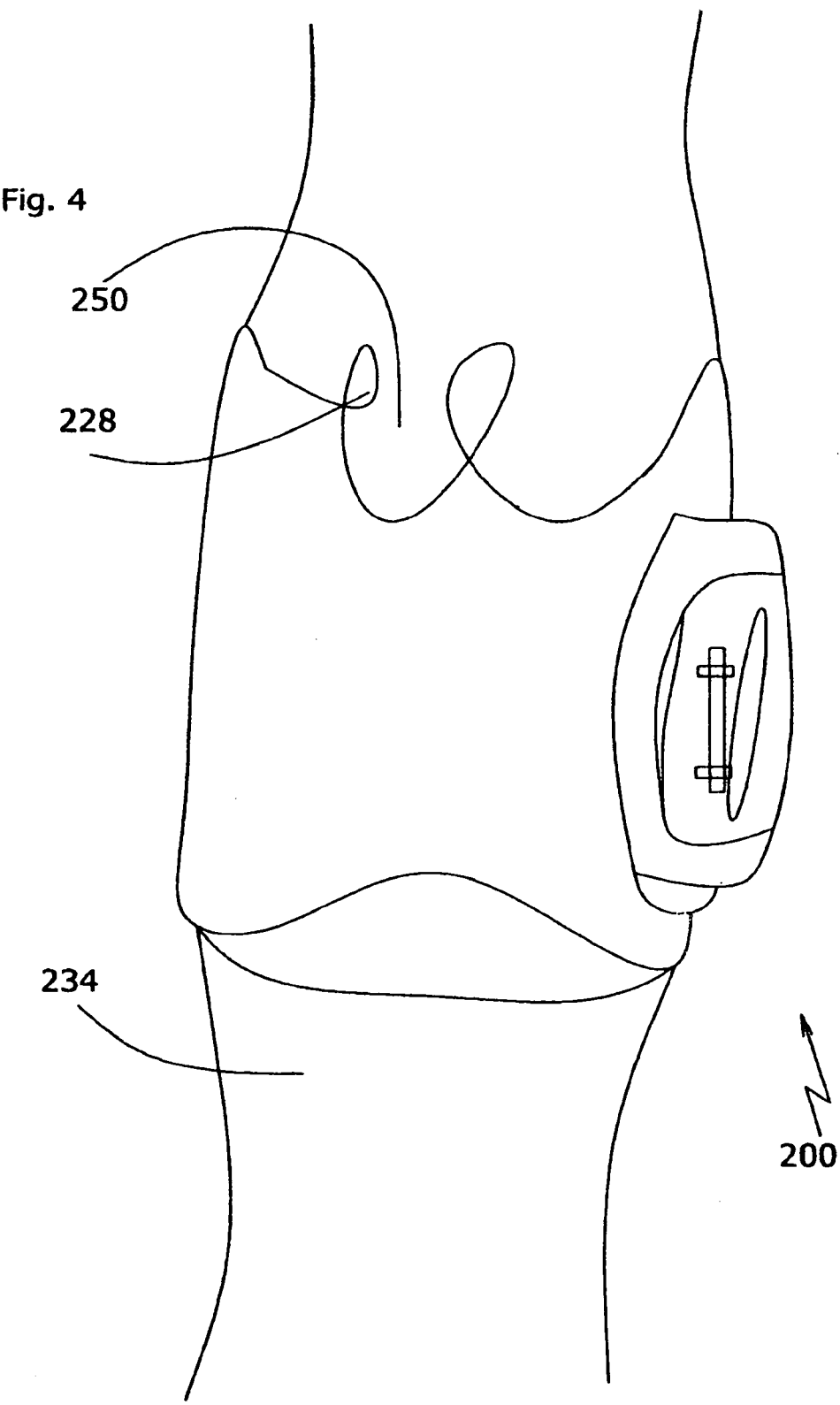
FIG. 4 is a perspective view of another preferred embodiment of a neuroprosthetic device, disposed on a lower leg, and having a locating system based on the tibial tuberocity.

FIG. 4 is a perspective view of a preferred embodiment of the neuroprosthetic leg device of the present invention, worn on the lower leg and having a locator based on the tibial tuberocity. Additional components of the locating system enable accurate positioning. A molding 228 of the anatomical shape of the inferior surface of tibial tuberocity 250 allows accurate location both of the longitudinal placement of device 200 along the long axis of lower leg segment 234, as well as the rotational orientation about the long axis of leg segment 234. Anatomical molding 228 is positioned by the user, abutting up against the tibial tuberosity 250, thus fixing leg device 200 accurately both the angular orientation around leg segment 234 and the position along the length of leg segment 234.

Figure 5:
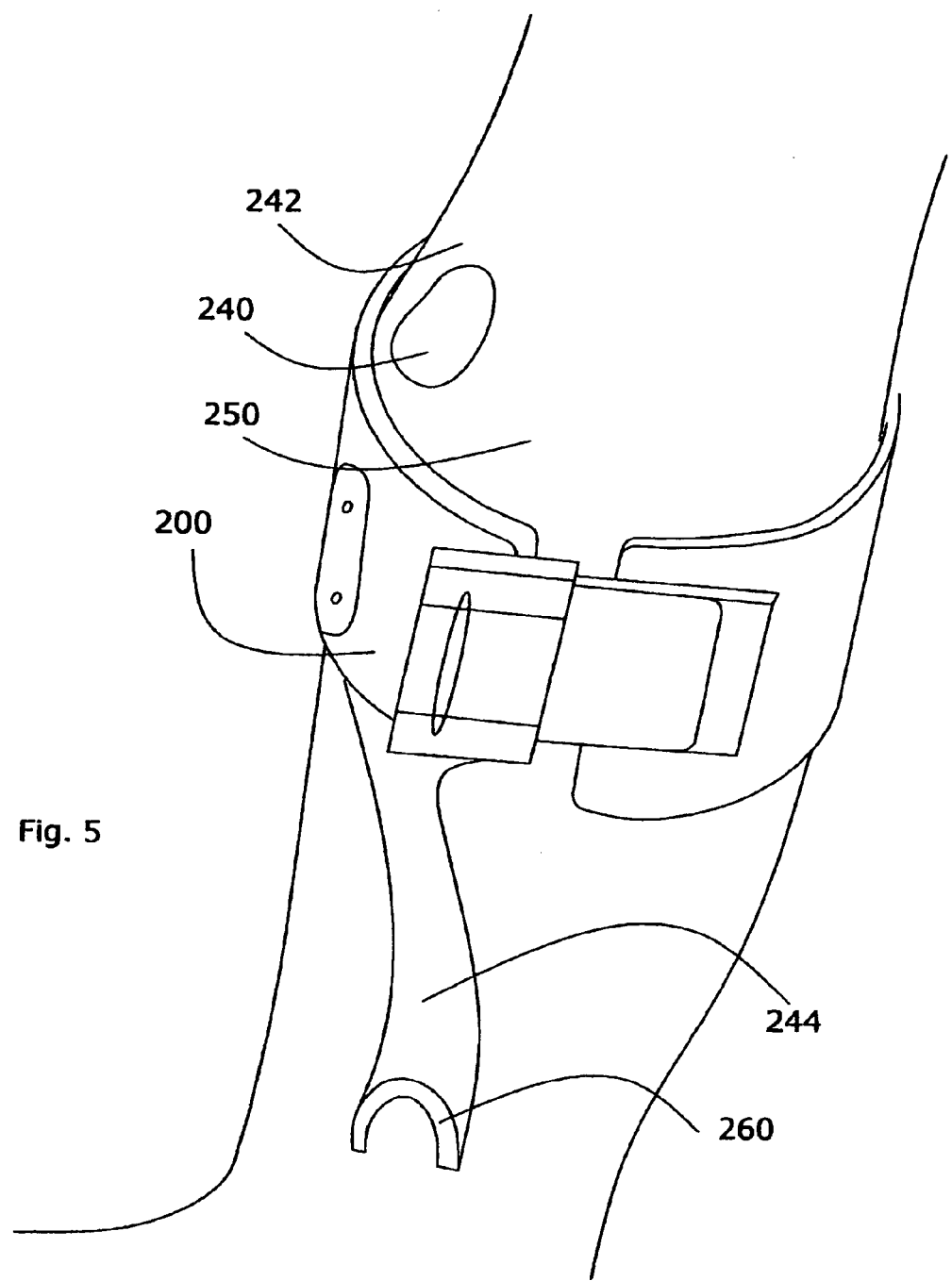
FIG. 5 is a perspective view of another preferred embodiment of a neuroprosthetic device, disposed on a lower leg, and having a locating system based on the patella.

In another preferred embodiment, shown in FIG. 5, moldings of other landmarks and features, in the vicinity of the placement site of device 200, include a patella locator 240 extending from the body of leg device 200, and abutting the inferior border of patella 242. Optionally, an additional locator 244, molded to fit over a malleolus 260 of an ankle joint, is also shown in FIG. 5. While locator 244, as illustrated, is used in conjunction with a lateral malleolus, it will be appreciated by one skilled in the art that a locator can also be used in conjunction with a medial malleolus.

Palpable features allow device 200 to be positioned by tactile feedback. Bony landmarks such as tibial tuberosity 250 (best seen in FIG. 4), patella 242, or malleolus 260 may be used to align tactile locators of leg device 200, such as patella locator 240, based on tactile feedback instead of, or in addition to, visual feedback.

Figure 6:
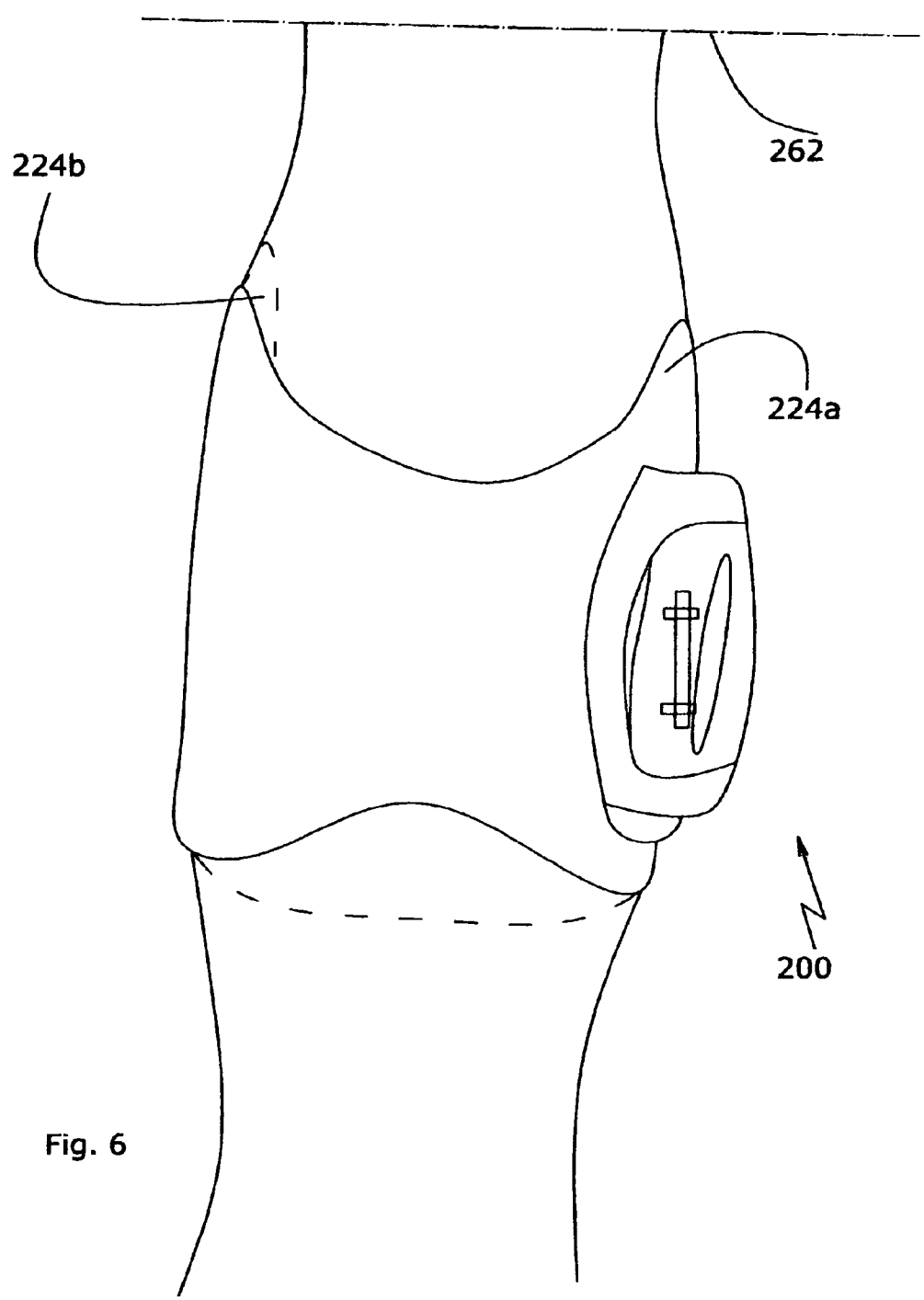
FIG. 6 is a perspective view of another preferred embodiment of a neuroprosthetic device, disposed on a lower leg, and having a locating system including flap finders.

Other components of the locating system, shown in FIG. 6, may include snug-fitting locator flaps 224a and 224b at each side of leg device 200. Locator flaps 224a and 224b point upward from leg device 200, utilizing knee joint axis of rotation 262 as a locating means. Articulation of the knee joint will result in the distal thigh segment touching the flaps 224a and 224b without bending them when device 200 is correctly located. When incorrectly located, one flap 224a or 224b will be bent outward by interacting with the thigh tissue. This will present tactile feedback to the user in the form of mechanical resistance to rotational adjustment of device 200, or visual feedback from bending of the locator flap 224a or 224b.

Figure 7:
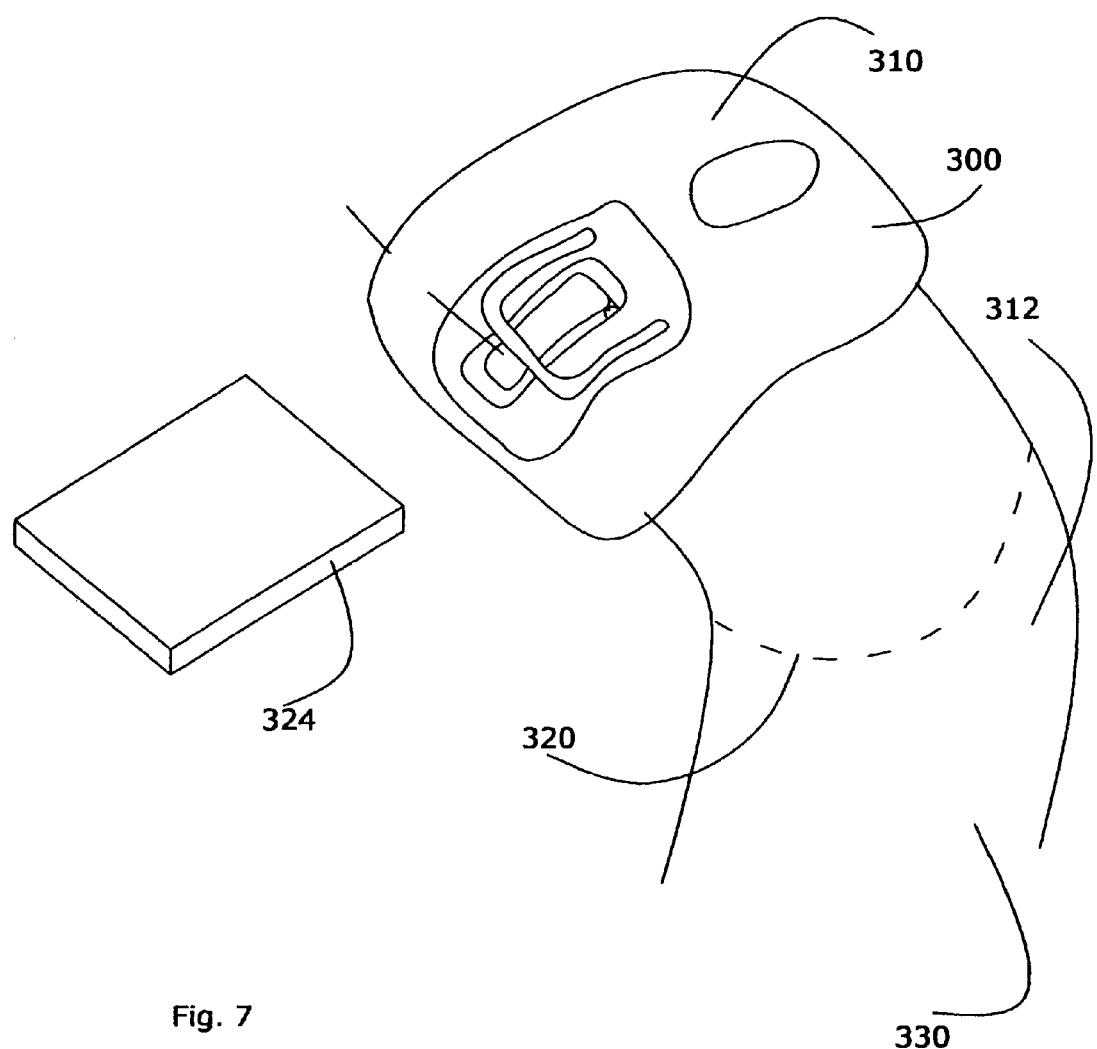
FIG. 7 is a perspective view of an inventive neuroprosthetic device, disposed on a thigh, for knee-joint activation.

An additional preferred embodiment, provided in FIG. 7, is a locating arrangement suitable for a neuroprosthetic thigh device 300 worn on a thigh segment 310 to activate a knee joint 312. The orientation of thigh device 300 is related to the orientation of a seat 324 of a chair (not shown) by a flat locator surface 320 on a posterior exterior surface of thigh device 300. While donning thigh device 300, locator surface 320 is aligned to seat 324 of the chair in which the user sits during donning, thereby fixing the orientation of thigh device 300 by using seat 324 as an external frame of reference. The user is trained to maintain a standard seated posture during the donning of thigh device 300, thereby constraining the orientation of thigh segment 310 about a longitudinal centerline thereof, and locating device 300 in orientation on to thigh segment 310.

It should be appreciated that similar types of locating devices may be used for locating a neuroprosthesis to other body sites. For example, a forearm/hand neuroprosthesis may be located, with a similar flat region, on the external palmar surface of the neuroprosthesis. This flat region locates to a flat reference plane such as a horizontal tabletop, together with the plane of the palm of the hand, during device donning.

Figure 8:
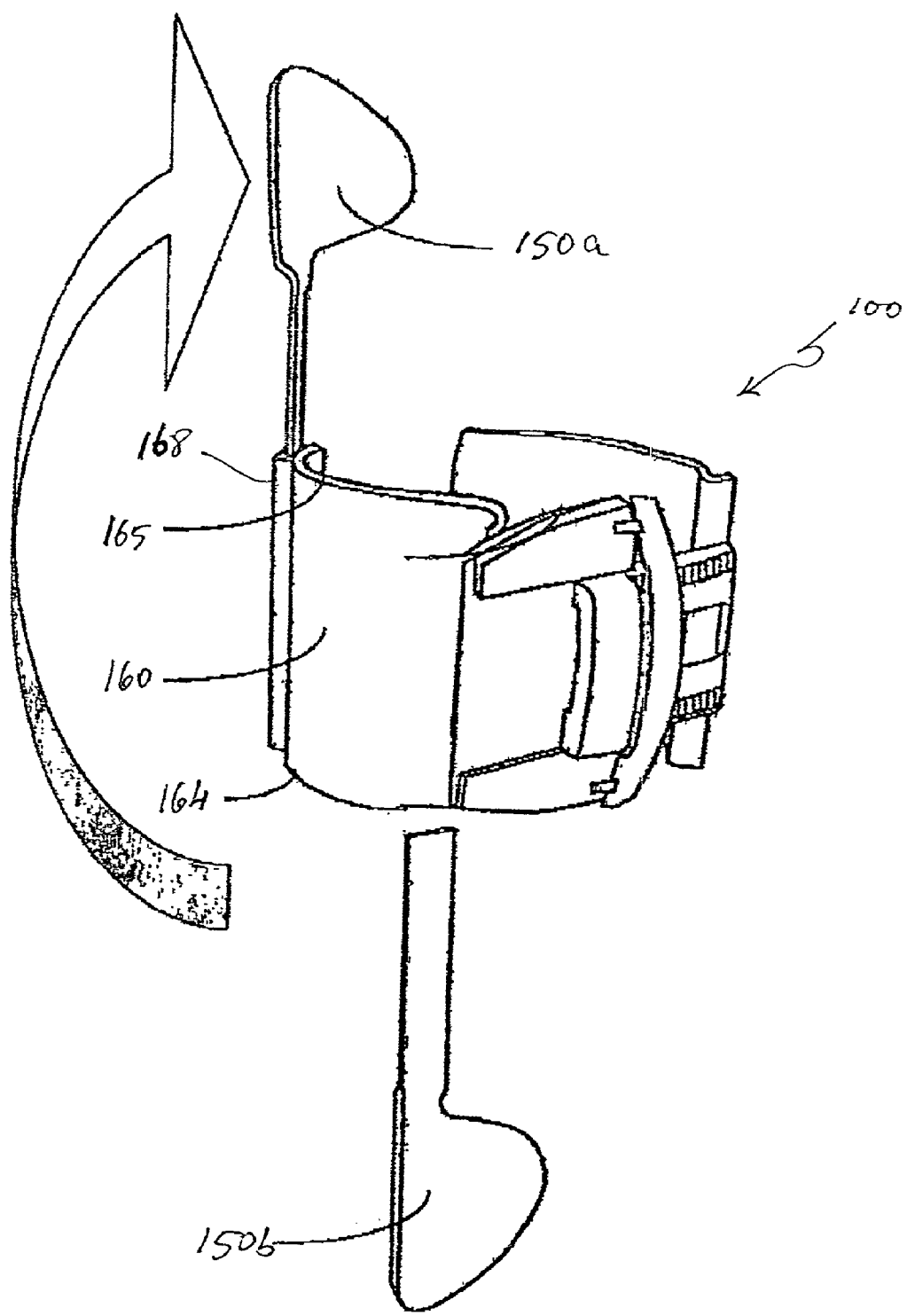
FIG. 8 is a perspective view of an inventive neuroprosthetic device having two removable flap finders.

Optionally, the neuroprosthetic devices may have removable locators, as shown in FIG. 8. FIG. 8 illustrates a tubular neuroprosthetic device 100 suitable for fitting to a conical body limb segment (not shown). Neuroprosthetic device 100, as shown in the drawing, is configured for activating a left arm, and is readily converted to a right-handed device by moving locating flaps 150a and 150b from inferior edge 164 of anterior panel 160 to superior edge 165 of the same anterior panel 160. Device 100 is rotated through 180° and donned on the (opposite) right arm to convert the original left-handed configuration to a right-handed one.

In FIG. 8, locating flap 150a has an arm for detachably sliding in and out of slot 168. This is of particular advantage in that locating flaps 150a and 150b can be removed after the location function has been performed, such that neuroprosthetic device 100 is not unwieldy and uncomfortable to use.

It will be appreciated that the length and width of flaps 150a and 150b can be adjusted or selected from a range of locator sizes during the device set-up procedure, in order to conform to an individual patient.

Figure 9:
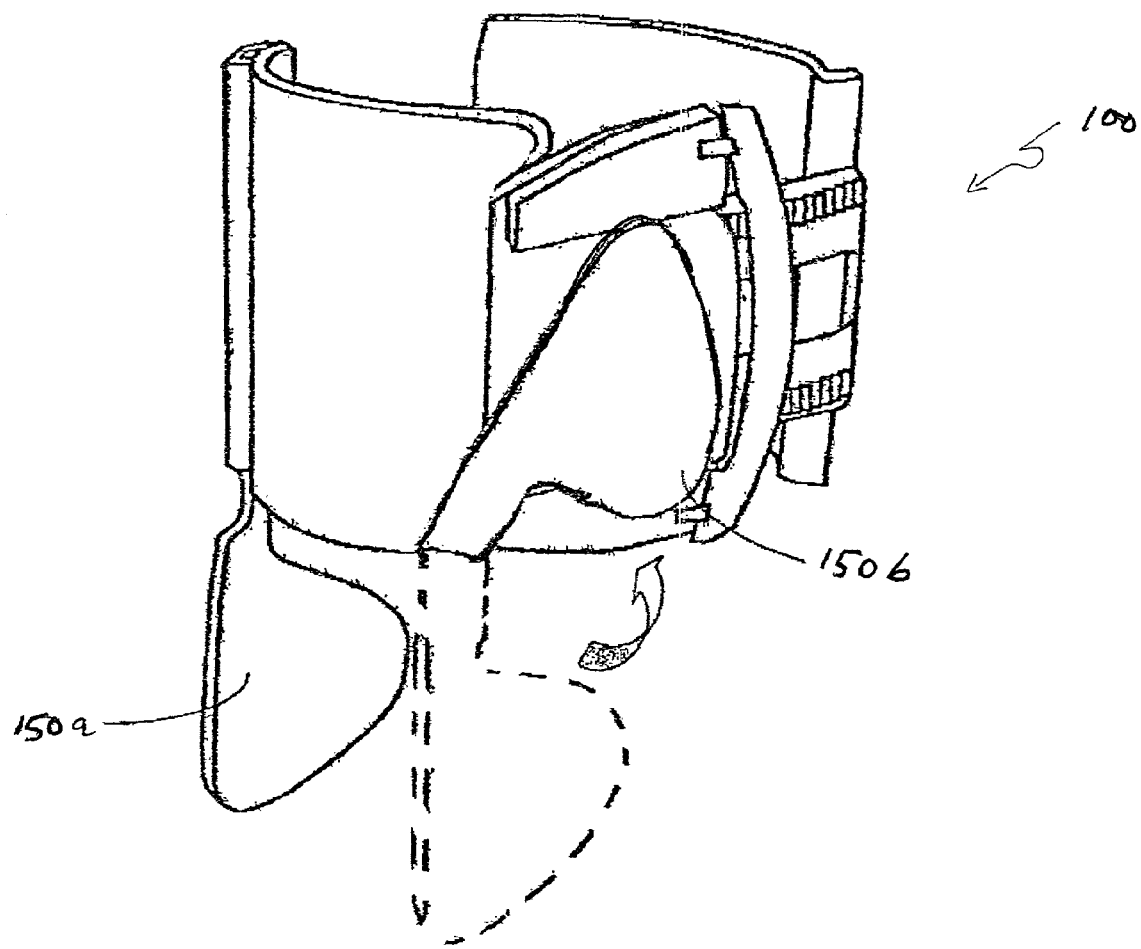
FIG. 9 is a perspective view of an inventive neuroprosthetic device having arrangements for moving the locator out of the way.

It may be preferable, in some cases, for the locating flaps to remain connected to the neuroprosthetic device after completing the locating function. FIG. 9 shows one arrangement for moving the locator out of the way, so that movement of the limb is not hampered. Locating flap 150a is shown in position during the donning of neuroprosthetic device 100 on a limb (not shown in the drawing). Locating flap 150b is shown in a folded-away position. It will be appreciated that various designs and configurations of the locating flaps can be contrived by one skilled in the art, including, but not limited to, telescopic collapsing of the locating flap or of the arm thereof.

The above-described device, and implementation method therefor, allow the surface electrode array to be manufactured in a fixed position within the surface neuroprosthetic device. In sharp contrast to the prior art, this enables pre-arranging the surface electrode array optimally, one electrode with respect to each other, and reduces the dependence on the high degree of skill, artistry, and experience required of the clinician to carry out the initial electrode set-up procedure.

The initial device set-up procedure is essentially reversed with respect to the prior art: the device housing the entire electrode array is placed on the limb and adjusted to the optimal position, then locator system is positioned and attached to the device, such that the device can be repeatably located to this optimal position by the patient.

Generally speaking, although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A surface neuroprosthetic device for functional electrical stimulation having a locating system for locating the device on to a conical limb segment of a user, the device comprising:

(a) an at least semi-rigid exoskeleton shell for encompassing at least a portion of the conical limb segment;

(b) at least one electrical stimulation electrode operatively connected with said shell, said electrode adapted so as to make electrical contact with a surface of the conical limb segment, so as to effect functional electrical stimulation (FES) of at least one muscle of the limb segment; and (c) a locator, operatively connected with said shell, for determining a positioning of said shell relative to the conical limb segment, such that said electrode is positioned near an activating point of said muscle, said locator including:

(i) a mechanism for determining circumferential positioning of said exoskeleton shell on the conical limb segment, and (ii) a mechanism for determining longitudinal positioning of said exoskeleton shell on the conical limb segment, and (iii) at least semi-rigid flaps extending outside a projection of a large face of said shell towards a limb portion of the limb segment, said flaps for locating said exoskeleton shell on each side of said limb portion, wherein the conical limb segment is selected from the group consisting of an upper arm and a lower leg, and wherein said limb portion is selected from the group consisting of an elbow and a knee.

2. The neuroprosthetic device of claim 1, wherein the conical limb segment is said upper arm, and said limb portion is said elbow.

3. The neuroprosthetic device of claim 1, wherein the conical limb segment is said lower leg, and said limb portion is said knee.

4. A surface neuroprosthetic device for functional electrical stimulation having a locating system for locating the device on to a lower leg of a user, the device comprising:

(a) an at least semi-rigid exoskeleton shell, designed and configured for disposing on the lower leg, said shell for encompassing a portion of the lower leg;

(b) at least one electrical stimulation electrode operatively connected with said shell, said electrode adapted so as to make electrical contact with a surface of the lower leg, so as to effect functional electrical stimulation (FES) of at least one muscle of the lower leg, and (c) a locator, operatively connected with said shell, for determining a positioning of said shell relative to the lower leg, such that said electrode is positioned near an activating point of said muscle, said locator including:

(i) a mechanism for determining circumferential positioning of said exoskeleton shell on the lower leg, and (ii) a mechanism for determining longitudinal positioning of said exoskeleton shell on the lower leg, wherein said mechanism for determining circumferential positioning and said mechanism for determining longitudinal positioning include a facing of said shell, said facing having a shape generally corresponding to an inferior border of a patella of the lower leg, said facing for abutting with said inferior border to determine said circumferential positioning and said longitudinal positioning of said shell on the lower leg.

5. The neuroprosthetic device of claim 4, wherein said facing has an adjusting and attaching mechanism for adjusting said facing to an optimal position to suit an individual patient and for attaching said facing in said position to the shell for subsequent location of the device by said patient on to the limb segment of said patient.

6. A surface neuroprosthetic device for functional electrical stimulation having a locating system for locating the device on to a conical limb segment of a user, the device comprising:

(a) an at least semi-rigid exoskeleton shell adapted to encompass at least a portion of the conical limb segment;

(b) at least one electrical stimulation electrode operatively connected with said shell, said electrode adapted so as to make electrical contact with a surface of the conical limb segment, so as to effect functional electrical stimulation (FES) of at least one muscle of the limb segment; and (c) a locator, operatively connected with said shell, for determining a positioning of said shell relative to the conical limb segment, such that said electrode is positioned near an activating point of said muscle, said locator including:

(i) a mechanism for determining circumferential positioning of said exoskeleton shell on the conical limb segment, and (ii) a mechanism for determining longitudinal positioning of said exoskeleton shell on the conical limb segment, wherein said mechanism for determining circumferential positioning of said exoskeleton shell includes at least semi-rigid flaps longitudinally extending outside a projection of a large face of said shell, said flaps configured so as to contact a surface of the limb segment when the device is correctly positioned on the limb segment, and wherein said flaps are configured so as to snugly contact a surface of the limb segment when said electrode is in a correct position near said activating point and such that rotation of the device away from said position results in a visually detectable deflection of said flaps.

7. The neuroprosthetic device of claim 6, wherein said shell is designed such that said flaps are for attaching to, and extending from, either longitudinal side of said shell, thereby enabling utilization of the device in both left-limb and right-limb applications.

8. A surface neuroprosthetic device for functional electrical stimulation having a locating system for locating the device on to a conical limb segment of a user, the device comprising:

(a) an at least semi-rigid exoskeleton shell adapted to encompass at least a portion of the conical limb segment;

(b) at least one electrical stimulation electrode operatively connected with said shell, said electrode adapted so as to make electrical contact with a surface of the conical limb segment, so as to effect functional electrical stimulation (FES) of at least one muscle of the limb segment; and (c) a locator, operatively connected with said shell, for determining a positioning of said shell relative to the conical limb segment, such that said electrode is positioned near an activating point of said muscle, said locator including:

(i) a mechanism for determining circumferential positioning of said exoskeleton shell on the conical limb segment, and (ii) a mechanism for determining longitudinal positioning of said exoskeleton shell on the conical limb segment, wherein said mechanism for determining circumferential positioning of said exoskeleton shell includes at least semi-rigid flaps longitudinally extending outside a projection of a large face of said shell, said flaps configured so as to contact a surface of the limb segment when the device is correctly positioned on the limb segment, and wherein said flaps are designed to retract into slots disposed within said shell.

9. The neuroprosthetic device of claim 8, wherein said flaps are disposed in said slots in a reversibly detachable fashion.

10. The neuroprosthetic device of claim 8, wherein said shell and said slots are designed such that said flaps are for attaching to, and extending from, either longitudinal side of said shell, thereby enabling utilization of the device in both left-limb and right-limb applications.

11. A surface neuroprosthetic device for functional electrical stimulation having a locating system for locating the device on to a conical limb segment of a user, the device comprising:
 (a) an at least semi-rigid exoskeleton shell adapted to encompass at least a portion of the conical limb segment;
 (b) at least one electrical stimulation electrode operatively connected with said shell, said electrode adapted so as to make electrical contact with a surface of the conical limb segment, so as to effect functional electrical stimulation (FES) of at least one muscle of the limb segment; and
 (c) a locator, operatively connected with said shell, for determining a positioning of said shell relative to the conical limb segment, such that said electrode is positioned near an activating point of said muscle, said locator including:
  (i) a mechanism for determining circumferential positioning of said exoskeleton shell on the conical limb segment, and
  (ii) a mechanism for determining longitudinal positioning of said exoskeleton shell on the conical limb segment,
wherein said mechanism for determining circumferential positioning of said exoskeleton shell includes at least semi-rigid flaps longitudinally extending outside a projection of a large face of said shell, said flaps configured so as to contact a surface of the limb segment when the device is correctly positioned on the limb segment, and wherein said flaps are designed and configured to be extended from said shell into an extended position during donning, and to be retracted towards said shell into a retracted position during use of the device.

12. The neuroprosthetic device of claim 11, said shell further including a securing mechanism for securing said flaps in said retracted position.

13. The neuroprosthetic device of claim 11, wherein said exoskeleton shell is designed to encompass at least a portion of a tower leg, and wherein said means for circumferential positioning and said mechanism for longitudinal positioning include at least one long flap extending down from said shell and over a malleolus of an ankle joint of said leg, so as to determine said circumferential and said longitudinal positioning of said shell on said leg.

14. The neuroprosthetic device of claim 13, said long flap having an adjusting and attaching mechanism for adjusting said mold to an optimal position to suit an individual patient and for attaching said mold in said position to the shell for subsequent location of the device by said patient on to the limb segment of said patient.

15. The neuroprosthetic device of claim 11, wherein said shell is designed such that said flaps are for attaching to, and extending from, either longitudinal side of said shell, thereby enabling utilization of the device in both left-limb and right-limb applications.

16. A surface neuroprosthetic device for functional electrical stimulation having a locating system for locating the device on to a conical limb segment of a user, the device comprising:
 (a) an at least semi-rigid exoskeleton shell adapted to encompass at least a portion of the conical limb segment;
 (b) at least one electrical stimulation electrode operatively connected with said shell, said electrode adapted so as to make electrical contact with a surface of the conical limb segment, so as to effect functional electrical stimulation (FES) of at least one muscle of the limb segment; and
 (c) a locator, operatively connected with said shell, for determining a positioning of said shell relative to the conical limb segment, such that said electrode is positioned near an activating point of said muscle, said locator including:
  (i) a mechanism for determining circumferential positioning of said exoskeleton shell on the conical limb segment, and
  (ii) a mechanism for determining longitudinal positioning of said exoskeleton shell on the conical limb segment,
wherein said mechanism for determining circumferential positioning of said exoskeleton shell includes at least semi-rigid flaps longitudinally extending outside a projection of a large face of said shell, said flaps configured so as to contact a surface of the limb segment when the device is correctly positioned on the limb segment, and wherein said exoskeleton shell is designed to encompass at least a portion of a lower leg, and wherein said mechanism for determining circumferential positioning and said mechanism for determining longitudinal positioning include a facing in said shell, said facing having a shape corresponding to an inferior border of a patella of said lower leg, said facing for abutting with said inferior border to determine said circumferential positioning and said longitudinal positioning of said shell on said lower leg.

17. The neuroprosthetic device of claim 16, wherein said facing has an adjusting and attaching mechanism for adjusting said facing to an optimal position to suit an individual patient and for attaching said facing in said position to the shell for subsequent location of the device by said patient on to the limb segment of said patient.

18. The neuroprosthetic device of claim 16, wherein said shell is designed such that said flaps are for attaching to, and extending from, either longitudinal side of said shell, thereby enabling utilization of the device in both left-limb and right-limb applications.

19. A method of locating a neuroprosthetic device on a conical limb segment of a user, the method comprising the steps of:
 (a) providing a neuroprosthetic device including:
  (i) an at least semi-rigid exoskeleton shell adapted to encompass at least a portion of the conical limb segment;
  (ii) at least one electrical stimulation electrode operatively connected with said shell, said electrode adapted so as to make electrical contact with a surface of the limb segment, so as to effect functional electrical stimulation (FES) of at least one muscle of the limb segment; and (iii) a locating system for positioning said shell relative to the limb segment, said locating system including:
   (A) a mechanism for determining circumferential positioning of said exoskeleton shell on the conical limb segment, and
   (B) a mechanism for determining longitudinal positioning of said exoskeleton shell on the conical limb segment;

(b) doming said neuroprosthetic device on the limb segment;

(c) applying said mechanism for determining circumferential positioning such that said neuroprosthetic device is circumferentially positioned near an activating point on the limb segment, and (d) applying said mechanism for determining longitudinal positioning such that said neuroprosthetic device is longitudinally positioned near said activating point on the limb segment, wherein said locating system further includes at least semi-rigid flaps longitudinally extending outside a projection of a large face of said shell, said flaps configured so as to contact a surface of the limb segment, the method further comprising the steps of:

(e) rotating the device in a vicinity of a potentially correct position on the limb segment;

(f) if said rotating the device results in substantially zero mechanical torsion resistance, identifying said position as a correct rotational position) and (g) if said rotating the device results in mechanical torsion resistance, reapplying step (c).

20. The method of claim 19, wherein said mechanism for determining circumferential positioning includes at least two at least semi-rigid flaps longitudinally extending outside a projection of a large face of said shell, and wherein the limb segment belongs to an upper arm.

21. The method of claim 20, wherein step (c) includes rotating an elbow joint of said arm from extension to flexion, and wherein, when the device is incorrectly positioned, a flexing of said elbow causes at least one of said flaps to be deflected outwards away from the limb segment by soft tissue of a proximal forearm associated with said upper arm.

22. The method of claim 19, wherein the limb segment belongs to a lower leg, wherein said mechanism for rotational positioning and said mechanism for longitudinal positioning include at least one long flap extending down from said shell and over a malleolus of an ankle joint of said leg, and wherein step (c) and step (d) include aligning said flap with said malleolus to circumferentially and longitudinally locate said shell on said leg.

23. A method of locating a neuroprosthetic device on a conical limb segment of a user, the method comprising the steps of:

(a) providing a neuroprosthetic device including:
   (i) an at least semi-rigid exoskeleton shell adapted to encompass at least a portion of the conical limb segment;
   (ii) at least one electrical stimulation electrode operatively connected with said shell, said electrode adapted so as to make electrical contact with a surface of the limb segment, so as to effect functional electrical stimulation (FES) of at least one muscle of the limb segment; and
   (iii) a locating system for positioning said shell relative to the limb segment, said locating system including:
      (A) a mechanism for determining circumferential positioning of said exoskeleton shell on the conical limb segment, and
      (B) a mechanism for determining longitudinal positioning of said exoskeleton shell on the conical limb segment;

(b) donning said neuroprosthetic device on the limb segment;

(c) applying said mechanism for determining circumferential positioning such that said neuroprosthetic device is circumferentially positioned near an activating point on the limb segment, and (d) applying said mechanism for determining longitudinal positioning such that said neuroprosthetic device is longitudinally positioned near said activating point on the limb segment, wherein said locating system further includes at least semi-rigid flaps longitudinally extending outside a projection of a large face of said shell, said flaps configured so as to contact a surface of the limb segment, the method further comprising the step of:

(e) rotating the device in a vicinity of a potentially correct position on the limb segment, wherein said mechanism for determining circumferential positioning include at least two at least semi-rigid flaps longitudinally extending outside a projection of a large face of said shell, and wherein the limb segment belongs to an upper arm, and wherein step (c) includes rotating an elbow joint of said arm from extension to flexion, and wherein, when the device is circumferentially aligned, proximal forearm tissue on said arm contacts said two flaps.

24. A method of locating a neuroprosthetic device on a conical limb segment of a user, the method comprising the steps of:

(a) providing a neuroprosthetic device including:
   (i) an at least semi-rigid exoskeleton shell adapted to encompass at least a portion of the conical limb segment;
   (ii) at least one electrical stimulation electrode operatively connected with said shell, said electrode adapted so as to make electrical contact with a surface of the limb segment, so as to effect functional electrical stimulation (FES) of at least one muscle of the limb segment; and
   (iii) a locating system for positioning said shell relative to the limb segment, said locating system including:
      (A) a mechanism for determining circumferential positioning of said exoskeleton shell on the conical limb segment, and
      (B) a mechanism for determining longitudinal positioning of said exoskeleton shell on the conical limb segment;

(b) donning said neuroprosthetic device on the limb segment;

(c) applying said mechanism for determining circumferential positioning such that said neuroprosthetic device is circumferentially positioned near an activating point on the limb segment, and (d) applying said mechanism for determining longitudinal positioning such that said neuroprosthetic device is longitudinally positioned near said activating point on the limb segment, wherein said locating system further includes at least semi-rigid flaps longitudinally extending outside a projection of a large face of said shell, said flaps configured so as to contact a surface of the limb segment, the method further comprising the step of:
  (e) rotating the device in a vicinity of a potentially correct position on the limb segment,
wherein the limb segment belongs to an upper arm, said mechanism for determining longitudinal positioning including at least semi-rigid flaps longitudinally extending outside a projection of a large face of said shell, wherein said flaps extend down from said shell and relate to epicondyles of an elbow of said arm to establish a longitudinal position along a long axis of the device.

25. A method of locating a neuroprosthetic device on a conical limb segment of a user, the method comprising the steps of:
  (a) providing a neuroprosthetic device including:
    (i) an at least semi-rigid exoskeleton shell adapted to encompass at least a portion of the conical limb segment;
    (ii) at least one electrical stimulation electrode operatively connected with said shell, said electrode adapted so as to make electrical contact with a surface of the limb segment, so as to effect functional electrical stimulation (FES) of at least one muscle of the limb segment; and
    (iii) a locating system for positioning said shell relative to the limb segment, said locating system including:
      (A) a mechanism for determining circumferential positioning of said exoskeleton shell on the conical limb segment, and
      (B) a mechanism for determining longitudinal positioning of said exoskeleton shell on the conical limb segment;
  (b) donning said neuroprosthetic device on the limb segment;
  (c) applying said mechanism for determining circumferential positioning such that said neuroprosthetic device is circumferentially positioned near an activating point on the limb segment, and
  (d) applying said mechanism for determining longitudinal positioning such that said neuroprosthetic device is longitudinally positioned near said activating point on the limb segment,
wherein said locating system further includes at least semi-rigid flaps longitudinally extending outside a projection of a large face of said shell, said flaps configured so as to contact a surface of the limb segment, the method further comprising the step of:
  (e) rotating the device in a vicinity of a potentially correct position on the limb segment,
wherein the limb segment belongs to a lower leg, wherein a mold in said shell has a shape corresponding to an inferior border of a patella of said leg, and wherein step (c) includes abutting said inferior border with said mold such that said neuroprosthetic device is circumferentially positioned on said leg.

26. A method of locating a neuroprosthetic device on a conical limb segment of a user, the method comprising the steps of:
  (a) providing a neuroprosthetic device including:
    (i) an at least semi-rigid exoskeleton shell adapted to encompass at least a portion of the conical limb segment;
    (ii) at least one electrical stimulation electrode operatively connected with said shell, said electrode adapted to make electrical contact with a surface of the limb segment, so as to effect functional electrical stimulation (FES) of at least one muscle of the limb segment; and
    (iii) a locating system for positioning said shell relative to the limb segment, said locating system including:
      (A) a mechanism for determining circumferential positioning of said exoskeleton shell on the conical limb segment, and
      (B) a mechanism for determining longitudinal positioning of said exoskeleton shell on the conical limb segment;
  (b) donning said neuroprosthetic device on the limb segment;
  (c) applying said mechanism for determining circumferential positioning such that said neuroprosthetic device is circumferentially positioned near an activating point on the limb segment, and
  (d) applying said mechanism for determining longitudinal positioning such that said neuroprosthetic device is longitudinally positioned near said activating point on the limb segment,
wherein said locating system further includes at least semi-rigid flaps longitudinally extending outside a projection of a large face of said shell, said flaps configured so as to contact a surface of the limb segment, the method further comprising the step of:
  (e) rotating the device in a vicinity of a potentially correct position on the limb segment,
wherein the limb segment belongs to a lower leg, wherein a mold in said shell has a shape corresponding to an inferior border of a patella of said leg, and wherein step (d) includes abutting said inferior border with said mold to longitudinally locate said shell on said leg.

27. A surface neuroprosthetic device for functional electrical stimulation having a locating system for locating the device on to a lower leg of a user, the device comprising:
  (a) an at least semi-rigid exoskeleton shell, adapted to encompass a portion of the lower leg;
  (b) at least one electrical stimulation electrode operatively connected with said shell, said electrode adapted so as to make electrical contact with a surface of the lower leg, so as to effect functional electrical stimulation (FES) of at least one muscle of the lower leg, and
  (c) a locator, operatively connected with said shell, for determining a positioning of said shell relative to the lower leg, such that said electrode is positioned near an activating point of said muscle, said locator including:
    (i) a mechanism for determining circumferential positioning of said exoskeleton shell on the lower leg, and
    (ii) a mechanism for determining longitudinal positioning of said exoskeleton shell on the lower leg,
wherein said mechanism for determining circumferential positioning and said mechanism for determining longitudinal positioning include a facing of said shell, said facing having a shape generally corresponding to an inferior border of a patella of the lower leg, said facing for abutting with said inferior border to determine said circumferential positioning and said longitudinal positioning of said shell on the lower leg.

* * * * *